US009297746B2

(12) United States Patent
Apperson et al.

(10) Patent No.: US 9,297,746 B2
(45) Date of Patent: Mar. 29, 2016

(54) ENERGETIC MATERIAL REACTION CHARACTERISTIC DETECTOR

(75) Inventors: Steven J. Apperson, Columbia, MO (US); Christopher J. Morris, Silver Spring, MD (US); Luke J. Currano, Columbia, MD (US); Collin R. Becker, Colorado Springs, CO (US); Madan Dubey, South River, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 843 days.

(21) Appl. No.: 13/308,631

(22) Filed: Dec. 1, 2011

(65) Prior Publication Data
US 2013/0143330 A1    Jun. 6, 2013

(51) Int. Cl.
*G01N 27/00* (2006.01)
*G01N 27/02* (2006.01)
*G01N 27/06* (2006.01)
*G01N 21/27* (2006.01)

(52) U.S. Cl.
CPC .............. *G01N 21/272* (2013.01); *G01N 27/02* (2013.01); *G01N 27/06* (2013.01)

(58) Field of Classification Search
CPC ..... G01N 27/06; G01N 30/96; G01N 27/021; G01N 27/3271; G01N 2030/965; G01N 33/5438; G01N 27/414; G01N 33/54373; G01N 25/4846; G01N 25/48; G01N 25/482; G01N 25/4866; G01N 27/16; G01N 25/54; G01N 27/00; G01N 27/02; B01J 8/001; B01J 35/0033; B01J 19/002; B01J 19/08; B01J 19/12; B01J 2219/00263; G01K 17/00; B82Y 15/00; F01N 3/00; F01N 11/002
USPC ................ 436/150, 147, 152, 156; 422/82.01
See application file for complete search history.

(56) References Cited

U.S. PATENT DOCUMENTS 7,608,478 B2    10/2009    Gangopadhyay et al.

FOREIGN PATENT DOCUMENTS

WO    WO 2007/053397 A2    5/2007

OTHER PUBLICATIONS

Apperson, Steven et al., "On-Chip Initiation and Burn Rate Measurements of Thermite Energetic Reactions", Mater. Res. Soc. Symp. Proc., 2006, pp. 1-6, vol. 896, 2006 Materials Research Society.
Bhattacharya, Shantanu et al., "A Novel On-Chip Diagnostic Method to Measure Burn Rates of Energetic Materials", Journal of Energetic Materials, 2006, pp. 1-15, vol. 24, Taylor & Francis LLC, ISSN: 0737-0652.
Becker, Collin R. et al., "Galvanic Porous Silicon Composites for High-Velocity Nanoenergetics", NANO Letters, 2011, pp. 803-807, vol. 11, ACS Publications, 2010 American Chemical Society.

*Primary Examiner* — Krishnan S Menon
*Assistant Examiner* — Dwan A Gerido
(74) *Attorney, Agent, or Firm* — Alan I. Kalb

(57) ABSTRACT

A reaction characteristic detector comprising a ladder assembly including a plurality of rungs, where each rung in the plurality of rungs comprises a reaction passage determiner spaced a distance from a point of an energetic material reaction initiation. Each reaction passage determiner has at least one characteristic that is configured to change in response to the reaction occurring proximate to the reaction passage determiner.

13 Claims, 4 Drawing Sheets

US 9,297,746 B2

ENERGETIC MATERIAL REACTION CHARACTERISTIC DETECTOR

GOVERNMENT INTEREST

Governmental Interest—The invention described herein may be manufactured, used and licensed by or for the U.S. Government.

FIELD OF THE INVENTION

The present disclosure relates to reaction characteristic detectors for energetic materials, including nanoenergetic materials.

BACKGROUND OF THE INVENTION

Energetic materials (EMs) provide the potential for significant advances in such microscale energy-demanding systems and applications as actuators, explosives, igniters, propulsion units, and power sources. Nanoscale EMs (nEMs), also known as nanoenergetic materials, offer the promise of much higher energy densities, faster rates of energy release, greater stabilities and probabilities against reaction, and more security (sensitivity to unwanted reaction initiation). The terms "nano" and "micro" are used by those skilled in the art rather arbitrarily to mean extremely small, such as at least one dimension within a range of tens to thousands of nanometers (a nanometer being a billionth of a meter). The concepts described herein are applicable to a variety of energetic materials as well as nanoenergetic materials.

Nano-energetic materials are mixtures of fuel and oxidizers closely packed together for a self-sustaining, high temperature reaction. Tiny particles have increased surface area over larger particles. Close proximity of the fuel and the oxidizer create waves of energy as the flame propagates through the solid material. Energy from adjacent layers ignites the fuel/oxidizer mixture. Material can be used as prepared or modified with polymers or explosives and used as a primers for explosives or propellants. Materials of this type have potential application in mining, demolitions, precision cutting, explosive welding, surface treatment and hardening of materials, pulse owner, crystallization and solar cells, sintering, micro-aerospace, satellite platforms, military applications and biomedical fields that destroy localized pathological tissues. Other prominent applications include thermite torches for underwater and atmospheric cutting or perforation, electronic hardware devices, additives to propellants and explosives having increased performance, pyrotechnic switches, airbag gas generator materials, high-temperature stable igniters, freestanding insertable heat sources, devices to breach ordnance cases to relieve pressure during fuel fires, thermal battery heat sources, incendiary projectiles, delay fuses, additives to propellants to increase burn rate without decrease of specific impulse and full sized shape-charged liners.

Some current technologies can be used to measure reaction characteristics such as propagation velocity. For instance, high speed cameras can measure reaction propagation velocity, but such high-speed cameras are relatively expensive and might be damaged in particularly hot, hostile, or caustic environments. Fiber optic based measurements require one data acquisition channel per measurement site, and thus tends to form a complex solution. It is desirable to limit the number of acquisition channels necessary to measure reaction propagation velocity.

Therefore, there is a need in the art for a detector for determining a characteristic of a reaction of an energetic material (including a nanoenergetic material).

BRIEF SUMMARY OF THE INVENTION

One embodiment of the invention comprises a reaction characteristic detector The detector includes a ladder assembly having a plurality of rungs, each rung in the plurality of rungs comprises a reaction passage determiner spaced a distance from a point of an energetic material reaction initiation. Each of the reaction passage determiner has at least one characteristic that changes in response to the reaction occurring proximate to the reaction passage determiner.

Another embodiment of the invention comprises a method of measuring characteristics of a reaction comprising: igniting a reaction of a energetic material; as the reaction becomes proximate a reaction passage determiner, determining a change in a characteristic of the determiner and determining at least one of a propagation time elapsed or distance traversed from ignition to occurrence of the change; and computing a reaction characteristic related to the change and the at least one of propagation time or distance.

BRIEF DESCRIPTION OF THE DRAWINGS

Embodiments of the present invention, briefly summarized above and discussed in greater detail below, can be understood by reference to the illustrative embodiments of the invention depicted in the appended drawings. The appended drawings, however, illustrate only typical embodiments of this invention and are therefore not to be considered limiting of its scope, for the invention may admit to other equally effective embodiments.

Figure 1:
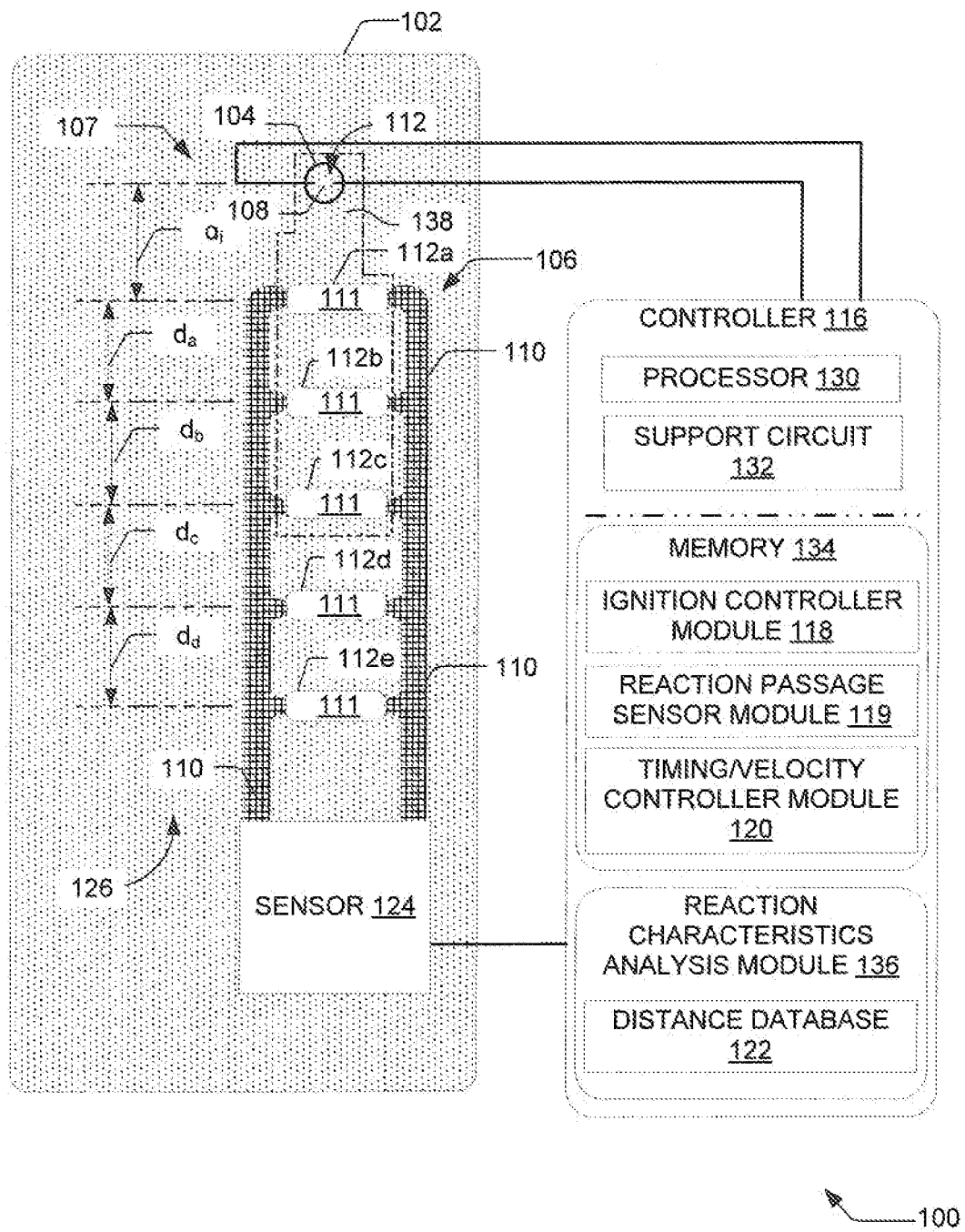
FIG. 1 is a block diagram of one embodiment of a reaction characteristic detector.

To facilitate understanding, identical reference numerals have been used, where possible, to designate identical or similarly functioning elements that are common to the figures. The figures are not drawn to scale and may be simplified for clarity. It is contemplated that elements and features of one embodiment may be beneficially incorporated in other embodiments without further recitation.

DETAILED DESCRIPTION OF THE INVENTION

FIG. 1 is a block diagram of one embodiment of a reaction characteristic detector 100 (hereinafter referred to as detector 100). Different embodiments of the detector 100 can be reusable, or alternately suitable to be used for one-time use only. Particular detector 100 should be designed to be suitably rugged for each particular energetic material being tested or likely to be encountered. Within this disclosure, including the claims, the term "energetic material" is a class of material with high amount of releaseably stored chemical energy. In this disclosure, typical classes of energetic materials comprise, e.g., explosives, pyrotechnic compositions, propellants (e.g., smokeless gunpowders and rocket fuels), and fuels (e.g., diesel fuel and gasoline). For example, the energetic material can, but does not have to, include a nanoporous silicon combined with an $NaClO_4$ oxidizer.

Certain embodiments of the detector 100 comprise a substrate 102 supporting a detection assembly 126 comprising an igniter 104, a ladder assembly 106, and a sensor 124. A variety of substances may be used as the substrate. The substrate 102 should be inert to the energetic material and be able to withstand the heat generated by a flame front. One such substrate material is glass Other substrates materials include silicon, silicon-on-insulator, RF4, carbide, fiberglass, perforated glass, LEXAN, polymers and/or other materials able to support formation of electronic circuits thereon and resist destruction during a reaction of the energetic material. The term "substrate" is not intended to be limited to a single supporting object, even though the singular form of the term is used. One or more supporting materials can form the substrate 102.

Prior to installation of any of the components, the substrate 102 should be cleaned to remove impurities that may affect the preparation of the apparatus or the properties of the energetic material. When glass is used as the substrate 102 material, it is generally cleaned with a corrosive acid solution such as Aqua Regis (a combination of concentrated sulfuric acid and concentrated nitric acid) or Piranha solution (a combination of concentrated sulfuric acid and hydrogen peroxide) to remove metals and organic contaminants. Residual acids or sulfates are removed by rinsing the substrate 102 under running distilled water. Cleaned substrates 102 are dried at suitable temperatures and pressures. Glass is suitably dried above 100° C., preferably at about 106° C. for about 15 minutes.

The detection assembly 126 is formed on the substrate 102 and is coupled to a controller 116 for activating a reaction within the detection assembly 126, collecting data as the reaction progresses, and analyzing the data to determine at least one characteristic of the reaction. Certain embodiments of the detection assembly 126 may be formed such as to be on at least one integrated circuit chip using thin film deposition techniques such as physical vapor deposition, chemical vapor deposition, masking, etching, and other well known microelectronic device fabrication techniques. Or, alternately, the detection assembly could be formed in a larger scale.

Certain embodiments of the detector 100 includes an energetic material deposition region 107 that receives an energetic material 138 over at least a portion of the ladder assembly 106 spreading at least from a point of reaction initiation 108 adjacent the igniter 104 to the ladder assembly 106 and, as shown, covering some or all of the ladder assembly 106. The amount of coverage of the ladder assembly 106 depends upon the type of testing being performed.

A molecular linker is coated onto the substrate 102 to bind the energetic material 138 to the substrate surface 102. The linker is able to bond with both fuel and oxidizer particles. In one embodiment, the binding sites are not random, but are spaced to non-randomly intermix the fuel and oxidizer for good interfacial surface area.

Suitable molecular-linker materials include polyvinyl pyrrolidone, poly(4-vinyl pyridine), poly(2-vinyl pyridine), poly (ethylene imine), carboxylated poly(ethylene imine) cationic poly(ethylene glycol) grafted copolymers, polyaminde, polyether block amide, poly(acrylic acid), cross-linked polystyrene, poly(vinyl alcohol), poly(n-isopropylacrylamide), copolymer of n-acryloxysuccinimide, poly(acrylontrile), fluorinated polyacrylate, poly(acrylamide), polystyrene-poly (4-vinyl)pyridine and polyisoprene-poly(4-vinyl)pyridine.

Metal oxide oxidizer (e.g. CuO etc) and metal fuel particles, such as aluminum particles, are sonicated in alcohol for a time sufficient to achieve homogenous dispersion. In one embodiment, the alcohol is 2-propanol, however, the use of other solvents that allow dispersion of the fuel and oxidizer. A polymer having a "pyridyl" group forms one embodiment of a molecular linker, and poly(4-vinyl pyridine), available from Aldrich Chemical, (Sigma-Aldrich Co., St. Louis, Mo.). In one embodiment, a solution is prepared having a concentration of about 0.0001-0.1% g/100 ml of the molecular linker in 2-propanol and is coated onto the substrate 102. Any suitable coating method is usable to coat the molecular linker solution, but spin-coating and dip-coating are typical.

The presence of material other than fuel and oxidizer tends to slow the burn rate of the energetic material 138. Cross-linking or bonding of the molecular linker with itself makes is difficult or impossible to remove excess polymer and reduces the burn rate. Thus, another feature of the molecular linker is that it does not bond with itself, allowing excess molecular linker polymer to be removed until essentially a monolayer of molecular linker remains.

After the molecular linker is coated onto the substrate 102, it is washed in ethanol, then annealed. If used, annealing takes place at temperatures of about 110° C. to about 160° C. for several hours. When the preferred poly(4-vinyl pyridine) molecular linker 40 is used, annealing takes place at about 120° C. for about 4 hours.

A wide variety of fuels are useful as part of the energetic material. Where the energetic particle is a thermite, the fuel is generally a metal. Such metals include aluminum, boron, beryllium, hafnium, lanthanum, lithium, magnesium, neodymium, tantalum, thorium, titanium, yttrium and zirconium. Metals having a relatively low melting temperature are useful so as to increase the speed at which they burn. The use of two or more metals, either physically mixed or alloyed, is contemplated.

The fuel is optionally formed into a shape, such as a sphere, that allows the fuel to bind compactly with the molecular linker. Sonication is one method for shaping the fuel particles. Fuel is placed in isopropanol and positioned within the sonic field. When activated, the sound waves disperse the fuel, creating extremely small particles that are often substantially monoparticles comprising a few atoms or molecules of fuel. The high degree of dispersion creates an extremely high fuel surface area. Other shapes, or larger particles, are useful in to applications where the extremely fast burn rate is not required.

The oxidizer should be selected to burn rapidly with the chosen fuel. The fuel and the oxidizer are chosen to assure that a self-propagating reaction takes place. As long as the fuel has a higher free energy for oxide formation than the oxidizer, an exothermic replacement reaction will spontaneously occur. Oxidizers include copper oxide (CuO or $Cu_2O$), silver oxide (AgO or $Ag_2O$), boron oxide ($B_2O_3$), bismuth oxide ($Bi_2O_3$), cobalt oxide (CoO), chromium oxide ($CrO_3$), iron oxide ($Fe_2O_3$), mercuric oxide (HgO), iodine oxide ($I_2O_5$), manganese oxide ($MnO_2$), molybdenum oxide ($MoO_3$), niobium oxide ($Nb_2O_5$), nickel oxide (NiO or $Ni_2O_3$), lead oxide (PbO or $PbO_2$), palladium oxide (PdO), silicone oxide ($SiO_2$), tin oxide (SnO or $SnO_2$), tantalum oxide ($Ta_2O_5$), titanium dioxide ($TiO_2$), uranium oxide ($U_3O_8$), vanadium oxide ($V_2O_5$) and tungsten oxide ($WO_3$).

Optimally, the amounts of fuel and oxidizer present in the thermite are in a stoichiometric ratio for combustion of the fuel with the oxidizer. In one embodiment, the ratios of fuel to oxidizer range from about 1.4 to about 1.8.

Certain embodiments of the ladder assembly 106 consist of a shaped electrode, or set of electrodes, that form rungs 112 extending and conductively coupled between two electrode rails 110. The reference character for the rungs 112a, 112b, 112c, 112d and 112e includes the appended letter to describe such relative aspects as direction of reaction, distance between adjacent electrode rungs and the like. The number of rungs 112a to 112e is a design choice that generally depends on the type of testing to be performed. Each rung 112a to 112e comprises a respective reaction passage determiner 111 being fabricated at respective prescribed distances from the point of reaction initiation 108. In one embodiment, the determiner 111 is a conductive strip of metal that becomes an open circuit when contacted with the heat of a reaction. Various embodiments of determiners 111 are described in detail with respect to FIGS. 4, 5 and 6 below.

The igniter 104 can be, but does not have to be, deposited on the same substrate 102, and using the same semiconductor processing steps as used to fabricate, the ladder assembly 106. Certain embodiments of the detector 100 can thus be formed with the igniter 104 on a separate chip from the ladder assembly 106, such, that the igniter 104 could be re-used or applied to ladder assemblies 106 with different configurations such as to test different energetic material. The characteristics and operations of electronic igniters such as 104 are generally well known for modern fuses, propellants, explosives, and the like. In one embodiment, igniter 104 comprises a pair of spaced apart electrodes 128 between which an electric arc can be created that is sufficient to initiate the reaction, such as the energetic material 138 catching fire. One illustrative experimental embodiment of igniter 104 includes an electrode pair 128 made of a tri-layer of approximately 200 angstroms chromium, 1000 angstroms platinum, and 3800 angstroms gold. A variety of configurations, materials, and dimensions of igniter is within the intended scope of the present disclosure. Another form of igniter is disclosed in U.S. Pat. No. 7,608,478 issued Oct. 27, 2009.

The reaction propagation velocity detector 100 quantifies reaction propagation of the energetic materials based on precise timing that successive reaction passage determiners 111 of the rungs 112a, 112b, 112c, 112d, and 112e undergo some quantifiable change that can be detected by the sensor 124. From the overall configuration of detector 100, the distance that each rung 112a, 112b, 112c, 112d, and 112e is from each other (as well as some point of a reaction initiation 108) is shown in FIG. 1 as $d_i$, $d_a$, $d_b$, $d_c$, and $d_d$, and is known or can be determined, and in certain embodiments may be stored in a database for use by the reaction characteristic determining computations. The determiners 111 have a design and/or composition to measure a particular reaction characteristic, e.g., velocity, acceleration, temperature, optical, pressure and the like.

In one embodiment, the detector 100 measures reaction velocity. The velocity is derived by dividing the distances shown as $d_i$, $d_a$, $d_b$, $d_c$, and $d_d$, (between pairs of points of the reaction passage determiner 111 or the reaction initiation 108) by the time to travel one or more distances. The timing can be derived between the point of reaction initiation 108 and any of the reaction passage determiners 111 associated with respective rungs 112a, 112b, 112c, 112d, and 112e; or alternately between any two rungs 112a, 112b, 112c, 112d, and 112e. Different numbers and configurations of the rungs 112a 112b, 112c, 112d, and 112e and their respective reaction passage determiners 111 (as well as the remainder of the ladder assembly 100), are intended to be within the intended scope of the present disclosure.

Different energetic materials are likely to undergo reactions at different temperatures, and react to yield different measurable characteristics e.g., reaction velocity, temperature, pressure and the like. As such, the materials, configurations, and positions of the rungs 112a, 112b, 112c, 112d, and 112e (and their respective reaction passage determiners 111) can be designed or selected not only based on the type of reaction and energetic materials being tested, but also the temperature ranges t which the energetic materials undergo reactions.

In one embodiment, the electrical characteristics of the respective reaction passage determiners 111 associated with the rungs 112a, 112b, 112c, 112d, and 112e change considerably during reaction passage during testing. The electrical characteristics of the rails 110 are not intended to change during the reaction, so any change during sensing by the sensor 124 can be considered a result of changes of the rungs 112a, 112b, 112c, 112d, and 112e (embodied by changes in the respective integrated reaction passage determiners 111). Different embodiments of the reaction passage determiners 111 are configured to rely on a variety of different mechanisms to provide such electrical changes, such as integrating thermocouples, consumable or breakable resistors, or electrical arcs as described below with respect to FIGS. 4, 5 and 6.

Certain embodiments of the detector 100 further includes the controller 116 to control operation, characteristics, timing and analysis performed by the detector 100.

In one embodiment, the controller 116 comprises a processor 130, memory 134, and support circuits 132. The processor 130 may be any commercially available microprocessor, microcontroller, application specific integrated circuit (ASIC) and/or the like that forms a general purpose computer and, when executing various software, becomes a specific purpose computer for controlling the detector 100. The processor 130 is coupled to support circuits 132 and memory 134. The support circuits 132 are well know circuits that facilitate operation of the processor 130, such as, for example, clock circuits, power supplies, busses, I/O circuits, network interfaces, cache, and the like.

Certain embodiments of the memory 134 include a random access memory (RAM) and/or read only memory (ROM) that together can store computer programs, operands, and other parameters that control the operation of certain embodiments of the controller 116. The memory 134 may also store data, information, test results, and the like that can be obtained, retained, or captured by the controller 116.

Certain embodiments of the controller 116 store in memory 134 a reaction characteristic analysis module 136 comprising an ignition controller module 118, a reaction passage sensor module 119 and a timing/ velocity controller module 120. In addition, in one embodiment, the memory 134 may store a distance database 122. The various modules 136, 118, 119, 120 and database 122 may, in actuality, be a number of different intertwined threads or processes using the resources of a stand-alone or networked processor, computer, processor, etc. Certain embodiments of the ignition controller module 118 are configured to control the timing of the energetic material ignition via the igniter 104. The reaction characteristic analysis module 136, using its constituent modules 118, 119, 120 and database 122, to monitor electrical characteristics (e.g., current, voltage, impedance, resistance, and the like) of the ladder assembly 106. The controller 116 is coupled to the sensor 124 that monitors the electrical characteristics of the ladder assembly 106. The operation of the reaction characteristic analysis module 136 and its constituent modules is described below with respect to FIG. 2.

Figure 2:
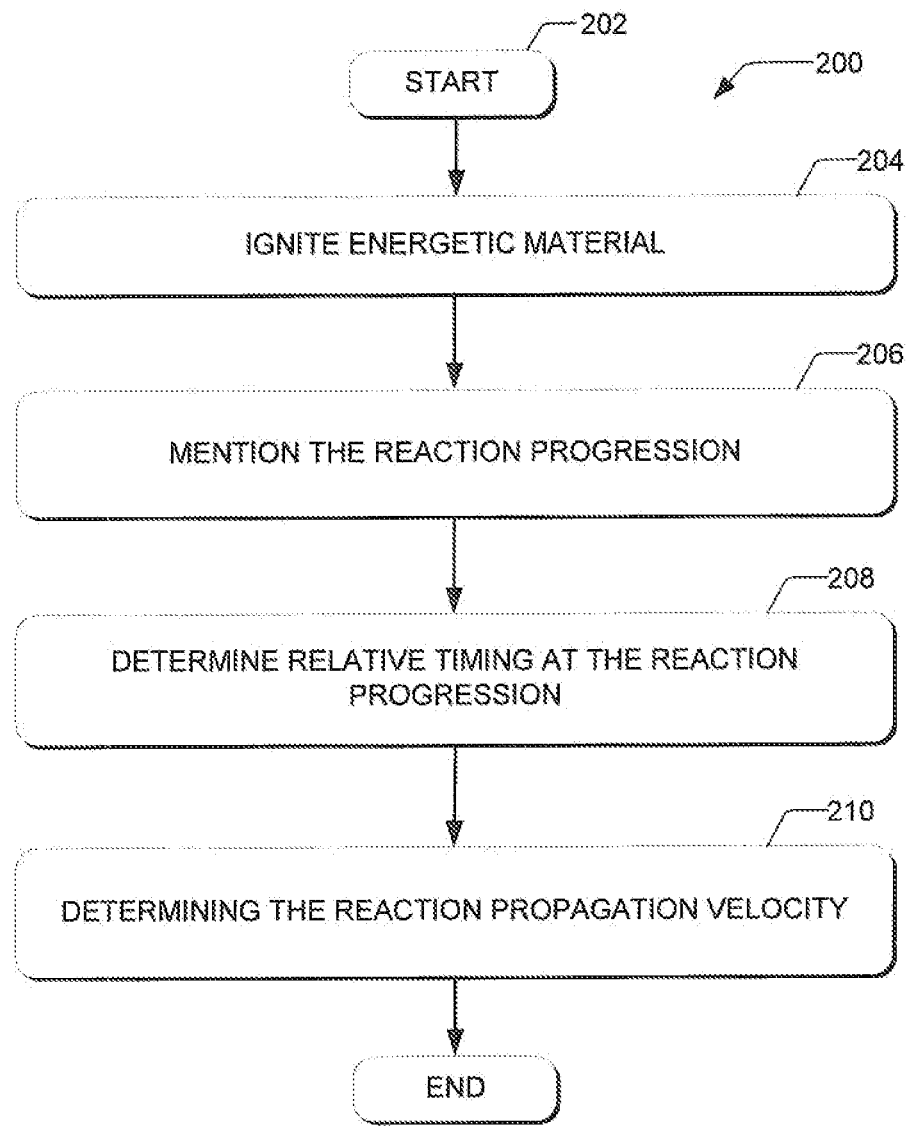
FIG. 2 is a flow diagram of a method for determining a reaction characteristic using the detector of FIG. 1.

FIG. 2 is a flow diagram of an embodiment of a method 200 for determining a reaction characteristic of an energetic material. The method 200 represents one implementation of the reaction characteristic analysis module 136. In this particular embodiment, the method 200 determines a reaction propagation velocity, i.e., the speed at which the reaction progresses from the ignition point across the ladder assembly. The method 200 begins at step 202 and proceeds to step 204.

At step 204, the ignition controller module 118 applies a voltage to the igniter 104 to ignite the energetic material. At step 206, (e.g., an implementation of the reaction passage sensor module 119), the method 200 monitors the progression of the reaction, as the reaction progresses along the ladder assembly 106 and becomes sequentially proximate each determiner 111, an electrical characteristic of the ladder assembly 106 changes (e.g., the resistance of the ladder assembly changes as a determiner is open circuited by the reaction). For instance, the particular change in resistance, or other related electrical characteristic, of the different embodiments of any of the reaction passage determiners 111 can be detected at the sensor 124. At step 208, the method 200 determines a relative timing of the reaction progression. For instance, based on the sensed change in electric characteristic monitored in step 206, the method determines the relative timing of reaction propagation, e,g., the amount of time for the reaction to progress from the ignition time to each change in electrical characteristic.

At step 210, the method 200 determines the reaction propagation velocity by determining the time for the reaction to travel the known distances from the igniter 104 to the various determiners 111. For instance, the method 200 may calculate a variety of reaction velocities based on the relative time of reaction between any two or more of the point of reaction initiator 108 and the determiners 111 Step 210 represents an exemplary implementation of the timing/velocity controller module 120.

In other embodiments, the method 200 may be used to determine reaction acceleration, reaction temperature profiles, reaction pressure profiles, reaction flash profiles and the like. Depending upon the determiner used, or combination of determiners, at least one of a time or distance based profile may be determined with respect to the reaction characteristic measured by the determiner.

Figure 3:
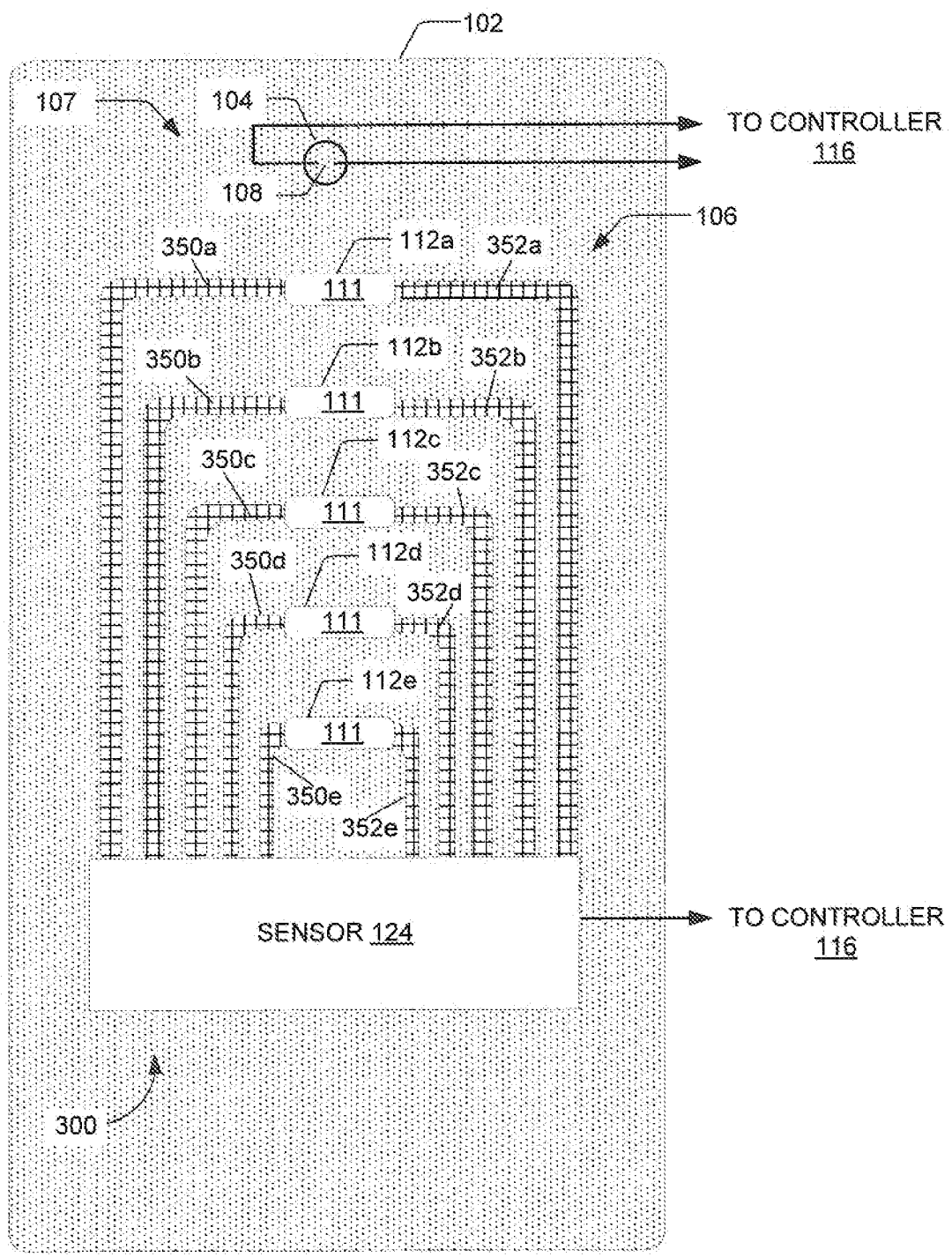
FIG. 3 is a block diagram of another embodiment of the reaction characteristic detector.

FIG. 3 is a plan view of an alternative embodiment of a detection assembly 300 supported upon a substrate 102. The detection assembly 300 comprises an igniter 704, a sensor 124, a plurality of rungs 112, where the rungs 112a, 112b, 112c, 112d, and 112e are individually electrically coupled at opposite ends to distinct individual pairs of electrical conductors 350a and 352a; 350b and 352b; 350c and 352c; 350d and 352d; and 350e and 352e. Both of the distinct individual pairs of all of the electrical conductors 350a and 352a; 350b and 352b; 350c and 352c; 350d and 352d; and 350e and 352e are each individually electrically coupled to the sensor 124. The sensor 124 monitors any change in an electrical characteristic of a determiner 111 associated with any of the distinct pairs of electrical conductors 350a and 352a; 350b and 352b; 350c and 352c; 350d and 352d; and 350e and 352e can be readily and individually detected. Certain embodiments of the method 200 of FIG. 2 can be similarly performed using the detection assembly 300 or 126 respectively of embodiments described with respect to either FIG. 3 or FIG, 1.

Figure 4:
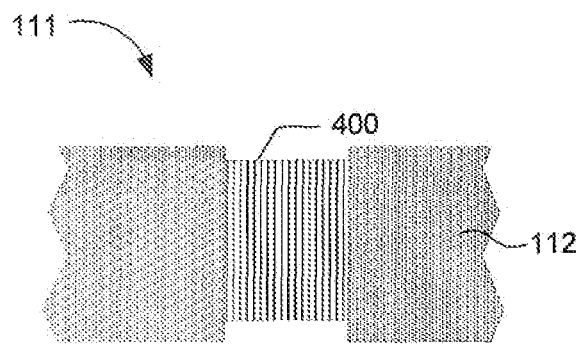
FIG. 4 is a plan view of one embodiment of a resistor embodiment as part of a ladder assembly of FIG. 1.
Figure 5:
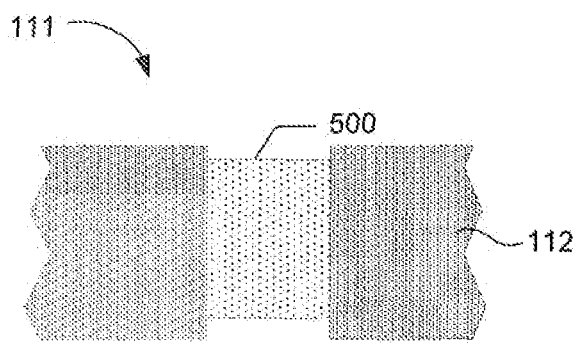
FIG. 5 is a plan view of another embodiment of a thermocouple junction embodiment as part of a ladder assembly of FIGS. 1.
Figure 6:
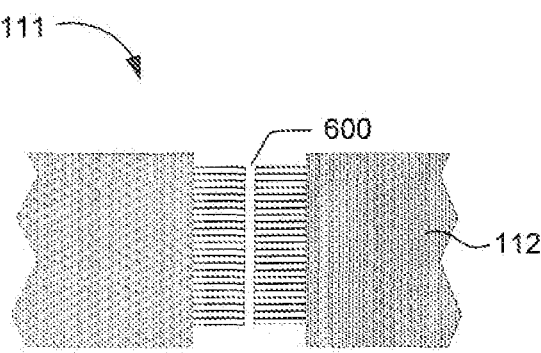
FIG. 6 is a plan view of yet another embodiment of a arc gap embodiment as part of a ladder assembly of FIG. 1.

A number of embodiments of the reaction passage determiner 111 are described with respect to FIGS. 4, 5 and 6, in which each rung 112a, 112b, 112c, 112d, and 112e may he used to determine passage of the reaction such as by monitoring the electrical characteristics of portions of the ladder assembly 106.

FIG. 4 is a plan view of one embodiment of one of the rungs 112a, 112b, 112c, 112d, or 112e as described with respect to FIG. 1 or 3. In this embodiment, the reaction passage determiner 111 integrates a resistor 400 that breaks, melts, or otherwise becomes more or less electrically resistive when the reaction passes the rung. In one embodiment, the resistor 230 is a thin film resistor. The same reference character "400" references each thin film resistor integrated into each of the five illustrated rungs 112a, 112b, 112c, 112d, and 112e. As the reaction alters each thin film resistor 400 for each successive rung 112a, 112b, 112c, 112d, and 112e, the corresponding electrical resistance for each respective rungs 112a, 112b, 112c, 112d, and 112e becomes very high, or even practically infinite. Current can flow only through those rungs 112a, 112b, 112c, 112d, and 112e that have not been reached by the reaction.

The ladder assembly 106 can be fabricated and/or metallized with the same materials and layer depths as those of the igniter 104, and can be fabricated simultaneously therewith. In one embodiment the rungs 112a, 112b, 112c, 112d, and 112e are straight and continuous at 50 μm wide coupled between 50 μm wide or wider rails 110. This configuration is designed such that a flame associated with the reaction propagation would break or consume a resistor 230 associated the electrode rungs 112a, 112b, 112c, 112d, and 112e and not alter the rails 110. For ease of computation, each thin film resistor 400 has a substantially identical cross sectional and length configuration, as well as incorporates identical materials, and therefore has substantially identical electrical resistance characteristics. This equal resistance configuration results in a predictably increasing larger change in resistance of the ladder assembly 106 as successive thin film resistors 400 are altered (e.g., open circuited). For example, assume that the ladder assembly 106 includes 10 electrode rungs. As the first of ten thin film resistors 400 is open circuited by the reaction, the number of current carrying rungs 112 are reduced to 90 percent of its original number and as such the resistance through the ladder assembly 106 increases by 11 percent. As the next thin film resistor 230 in its respective rung 112 opens leaving eight rungs 112 electrically operational, the resistance of the ladder assembly 106 increases by 12.5 percent of the value when there were nine rungs 112 intact. The resistance continues to increase as each successive resistor is opened by propagation of the reaction. In absolute terms, assume that each rung 112 has a resistance of 10 ohms, then the total ladder assembly 106 with ten electrode rungs 112 would have a resistance of 1 ohm. Opening the first of ten thin film resistors 230 would increase the total resistance of the electrode ladder assembly 106 from 1 to 1.11 ohm. Each successively opened resistor increases the ladder assembly resistance by a measurable amount. In one embodiment, the sensor may drive the ladder assembly with a fixed voltage and measure the current change as the resistance of the ladder assembly incrementally increases with time. In other embodiments, the resistance values may be different in each rung such that the current changes are equal with the opening of each resistor. Other current profiles may be found useful and can be formed through varying the resistor values.

In one embodiment, the detection assembly 300 or 126 may be disposable after use. In other embodiments, the detection assembly may be cleaned and the thin film resistors replaced to form a reusable detection assembly.

FIG. 5 is a plan view of another embodiment of the reaction passage determiner 111 comprising a thermocouple junction

500. As a generally known temperature sensor, each thermocouple includes a junction between two different metals that produces a voltage related to a temperature difference. Each thermocouple junction 500 alters its electric conductivity as the reaction initiated by the igniter 104 passes by each respective rung, thus raising the temperature proximate the thermocouple junction 500. As such, as the reaction alters an electrical characteristic of each thermocouple junction 232, the corresponding electrical resistance for each respective rung 112 increases. In this embodiment, reaction propagation velocity is measured in a similar manner as used with a determiner 111 fabricated from a thin film resistor or metallization. In other embodiments, the thermocouple junctions may be altered to enable each change to indicate absolute or relative temperature change at each rung. In this manner, the thermocouple junctions may be used to determine a temperature profile (e.g., temperature versus distance or time) for the reaction.

FIG. 6 is a plan view of yet another embodiment of reaction propagation determiner 111 comprising a arc gap 600. Certain embodiments of the arc gap 600 alter its electric conductivity when the reaction passes by each respective rung containing the arc gap 600. The arc gaps 600 are each formed with a small gap between two electrodes (e.g., about 30 μm, or in the range from 10 μm to 100 μm, in certain embodiments, and within a range of several orders of magnitude greater or less than this value) are configured to take advantage of the reaction zone. In one embodiment, the gap is formed by etching a space in the rung. In other embodiments, the gap may be formed during deposition of the ladder assembly using a mask to define a gap in rung metallization, If a voltage of 20-30v (but could also be more or less) is applied to the ladder assembly 106, then when the reaction crosses each arc gap 600 electrical breakdown occurs. The breakdown facilitates current flow through the gap. Such electrical breakdown and current flow would be detectable by certain embodiments of the sensor and controller 116 to determine the velocity of the reaction propagation. As such, as the reaction alters an electrical characteristic of each arc gap 600 e.g., decreases electrical resistance for each respective rung 112a, 112b, 112c, 112d, and 112e. Such measurements of resistance when different arc gaps 234 change states, and associated calculations, can be performed by a variety of embodiments of the controller 116 as described above. In some embodiments, the increase in current may be transient as the reaction passes an arc gap. As such, steady state current into the ladder assembly may not increase with time. As such, the controller measures the number of current spikes and time of each occurrence of each current spike. In this manner, reaction propagation characteristics can be determined.

The foregoing embodiments measured reaction characteristics such as temperature and velocity. These determiners (e.g., metallization, resistive, thermocouple and arc gap) may also be used to determine reaction acceleration. Other determiners may be used to measure reaction pressure profiles and/or optical (Flash) profiles using pressure or optical sensors as the determiners. Those skilled in the art may determine other determiners that are within the scope of this invention.

In various alternative embodiments, spacing of the rungs may be non-uniform (e.g., logarithmic, linear increasing, linear decreasing and the like. Also, determiners may be varied along the ladder assembly, e.g., intermixing arc gap with thermocouple, resistive, pressure optical, metallization, and the like.

Various elements, devices, modules and circuits are described above in association with their respective functions. These elements, devices, modules and circuits are considered means for performing their respective functions as described herein.

While the foregoing is directed to embodiments of the present invention, other and further embodiments of the invention may be devised without departing from the basic scope thereof.

What is claimed is:

1. A reaction characteristic detector, comprising:
a ladder assembly including a plurality of rungs, each rung in the plurality of rungs comprises a reaction passage determiner spaced a distance from a point of an energetic material reaction initiation wherein each reaction passage determiner has at least one characteristic that changes in response to the reaction occurring proximate to the reaction passage determiner on a silicon chip integrated with other electronics said reaction passage determiner being a thermocouple.

2. The reaction characteristic detector of claim 1, further comprising a sensor for detecting if the reaction is proximate to a reaction passage determiner based on a distinct reaction passage determiner changing at least one characteristic.

3. The reaction characteristic detector of claim 1, comprising an ignition controller module to control timing of an ignition at a point of reaction initiation.

4. The reaction characteristic detector of claim 1, comprising a reaction passage determiner controller module for determining when a reaction passes each reaction passage determiner.

5. The reaction characteristic detector of claim 1, comprising a reaction passage sensor module for sensing a characteristic of a reaction passage determiner to indicate when a reaction has passed the reaction passage determiner.

6. The reaction characteristic detector of claim 1, comprising a database to store at least one of a distance between each reaction passage determiner or a distance between each reaction passage determiner and the point of reaction initiation.

7. The reaction characteristic detector of claim 1 wherein each rung in the plurality of rungs is individually connected to a sensor.

8. The reaction characteristic detector of claim 1, comprising a controller for determining a characteristic of the energetic material reaction.

9. The reaction characteristic detector of claim 8 wherein the characteristic comprises at least one of velocity, acceleration, pressure, temperature, or optical.

10. The reaction characteristic detector of claim 1, wherein the ladder assembly comprises a pair of rails electrically connected to opposite ends of all the rungs.

11. The reaction characteristic detector of claim 10, wherein the sensor is electrically connected to the rails.

12. The reaction characteristic detector of claim 1, wherein the ladder assembly is supported on a substrate.

13. The reaction characteristic detector of claim 12, wherein the substrate further supports an igniter located at the point of initiation.

* * * * *